(12) United States Patent
Hively et al.

(10) Patent No.: US 6,484,132 B1
(45) Date of Patent: Nov. 19, 2002

(54) CONDITION ASSESSMENT OF NONLINEAR PROCESSES

(75) Inventors: Lee M. Hively, Philadelphia, TN (US); Paul C. Gailey, Athens, OH (US); Vladimir A. Protopopescu, Knoxville, TN (US)

(73) Assignee: Lockheed Martin Energy Research Corporation, Oak Ridge, TN (US)

( * ) Notice: Subject to any disclaimer, the term of this patent is extended or adjusted under 35 U.S.C. 154(b) by 0 days.

(21) Appl. No.: 09/520,693

(22) Filed: Mar. 7, 2000

(51) Int. Cl.$^7$ ................................................. A61B 5/00
(52) U.S. Cl. ....................... 702/190; 702/189; 702/191; 600/544; 600/545
(58) Field of Search ................................ 702/179, 180, 702/181, 182, 183, 184, 185, 186, 187, 188, 189, 190, 191–199, 58, 59, 60–74; 600/544, 545

(56) References Cited

U.S. PATENT DOCUMENTS

| | | | |
|---|---|---|---|
| 3,863,625 A | * 2/1975 | Viglione et al. | 128/2.1 |
| 5,311,876 A | * 5/1994 | Olsen et al. | 128/731 |
| 5,339,826 A | * 8/1994 | Schmidt et al. | 128/731 |
| 5,349,962 A | * 9/1994 | Lockard et al. | 128/732 |
| 5,626,145 A | 5/1997 | Clapp et al. | 128/731 |
| 5,655,540 A | * 8/1997 | Seegobin | 128/702 |
| 5,743,860 A | 4/1998 | Hively et al. | 600/544 |
| 5,815,413 A | * 9/1998 | Hively et al. | 364/574 |
| 5,857,978 A | * 1/1999 | Hively et al. | 600/544 |
| 5,995,868 A | * 11/1999 | Dorfmeister et al. | 600/544 |
| 6,192,317 B1 | * 2/2001 | Yazici et al. | 702/58 |
| 6,230,049 B1 | * 5/2001 | Fischell et al. | 600/544 |
| 6,304,775 B1 | * 10/2001 | Iasemidis et al. | 600/544 |

* cited by examiner

Primary Examiner—Marc S. Hoff
Assistant Examiner—Jeffrey R. West
(74) Attorney, Agent, or Firm—Quarles & Brady LLP

(57) ABSTRACT

There is presented a reliable technique for measuring condition change in nonlinear data such as brain waves. The nonlinear data is filtered and discretized into windowed data sets. The system dynamics within each data set is represented by a sequence of connected phase-space points, and for each data set a distribution function is derived. New metrics are introduced that evaluate the distance between distribution functions. The metrics are properly renormalized to provide robust and sensitive relative measures of condition change. As an example, these measures can be used on EEG data, to provide timely discrimination between normal, preseizure, seizure, and post-seizure states in epileptic patients. Apparatus utilizing hardware or software to perform the method and provide an indicative output is also disclosed.

12 Claims, 6 Drawing Sheets

CONDITION ASSESSMENT OF NONLINEAR PROCESSES

STATEMENT OF GOVERNMENT RIGHTS

This invention was made with Government support under Contract No. DE-AC05-96OR22464 awarded by the U.S. Department of Energy to Lockheed Martin Energy Research Corporation, and the Government has certain rights in this invention.

FIELD OF THE INVENTION

The current invention relates to methods and apparatus for analyzing nonlinear data and particularly time-series nonlinear data derived from any of a variety of nonlinear processes or processes having a nonlinear component, and more particularly relates to methods and apparatus for detecting and measuring changes in states of nonlinear systems, conditions of nonlinear processes, and structure of nonlinear data.

BACKGROUND OF THE INVENTION

Nonlinear processes, from which nonlinear data can be derived, are ubiquitous. The number and kind of such processes cannot be fully listed, but examples include: brain waves; heart waves;

electrical transients in power systems; fluid (air or water) flow over surfaces such as those of automobiles, airplanes, or submarines; weather and climate dynamics; machine tool-part interaction (e.g., tool chatter); nuclear reactor instabilities; fusion plasma instabilities; earthquakes; turbulent flow in conduits; fatigue and stress crack growth; and planetary or satellite motion. Applications in such fields as engineering, medicine, and research frequently require the ability to distinguish and/or quantify differences between apparently similar, but actually different, states in a nonlinear system. Inherent nonlinearity and high levels of noise in systems such as those described by example above make condition or state comparisons extremely difficult or even impossible through the use of linear or traditional nonlinear analyses. For example, conventional methods cannot detect differences in brain wave activity between baseline, pre-seizure, seizure, or postseizure states. Timely monitoring and detection of changes in the state of a nonlinear system can be used to provide adequate metrics for the basic purpose of better understanding the process. From a practical standpoint, detecting and measuring condition changes can be used predictively, for example, to detect the imminent onset of a seizure or an imminent failure of the system or a part thereof. The process may need to be monitored in real-time or near real-time for the monitoring to be of use. Conventional methods, in those instances where they can be of use, however, require a relatively large amount of data and a relatively large amount of computing power. This makes real-time monitoring difficult or impossible simply because of the cost or availability of the data acquisition, storage, and manipulation means.

Even existing nonlinear methods of monitoring process data cannot always detect differences on the scale required for a given process. In some cases, this is simply because the method is insufficiently sensitive, or the measurements of the changes in state or condition are not robust enough to be reliable. In other cases, the methods require large amounts of storage and computing capability that are not available as a practical matter, or at all.

OBJECTS OF THE INVENTION

It is an object of the current invention to overcome the above-mentioned problems by providing a method and apparatus for detecting, measuring, and monitoring condition changes in nonlinear processes and systems.

It is also an object of the current invention to provide a method and apparatus capable of providing an indication of a difference between two similar but different states in nonlinear processes and systems.

It is a further object of the current invention to provide a means of monitoring and comparing nonlinear data from a process or system to provide an indication of a change in state or condition of the process or system.

It is moreover an object of the current invention to provide a method and apparatus of measuring and detecting trends in the condition or state of a nonlinear process or system.

In accordance with the foregoing objectives, it is also a particular object of this invention to provide a method and apparatus for filtering, monitoring, and comparing nonlinear data from a process or system to provide an indication of a change in state or condition of the process or system, wherein said filtering, monitoring, comparing, and detecting are based solely on the data derived from the process or system in the absence of any assumptions about or models for the underlying process or system dynamics.

In a specific aspect of the invention, it is an object thereof to provide a method and apparatus for filtering, monitoring, and comparing nonlinear data from EEG sensors, and particularly from a single channel of scalp EEG, to detect and monitor nonseizure, pre-seizure, and seizure epileptic states such that a forewarning of a seizure may be provided.

The invention accomplishes the foregoing and other objects by providing a method in which nonlinear data from a process or system is acquired, monitored, and filtered. The filtered data are then used to represent the system dynamics as connected phase-space points, in turn represented by 2n-dimensional vectors within a windowed data set. A distribution function is calculated for each windowed data set to capture the occurrence frequency in the discretized (connected) phase-space. Condition change is detected, monitored, and measured by comparing the distribution functions via dissimilarity metrics, specifically using $\chi^2$ statistics and $L_1$ distance. The dissimilarity measures are renormalized to provide a consistent comparator for robust and reliable detection of changes or trends. The method can be incorporated into apparatus including a data collector, a processor, and an output device enabling real-time and near real-time assessment of data. The apparatus can be made automatic, that is, made to provide an output only when a change or given magnitude of change is detected.

The method provides a new, timely, accurate, and robust means for measuring condition change in nonlinear data. It is model-independent and, by appropriate selection of comparison criteria, can be used to detect or measure any selected amount or degree of change in a system.

SUMMARY OF THE INVENTION

In accordance with one aspect of the invention, the foregoing and other objects are achieved by a method for detecting or measuring condition or state changes in a nonlinear process or system, or monitoring the condition or state of a nonlinear process or system. The method comprises the following steps. A channel of nonlinear data from the process or system is provided. The data, referred to herein as e-data, may be provided in real-time or near real-time or may be from a means for data storage. While the e-data is typically a time serial sequence of nonlinear measures, the method is not limited to the use of time serial sequence measures, but may be used with data sequenced by a means other than time. The e-data is then filtered by means of a zero-phase quadratic filter that removes artifacts (f-data) from the data without distorting the phase or amplitude of the e-data. The resulting artifact-filtered data is referred to as g-data. The g-data is serially discretized into windowed cutsets. For time serial data, the cutsets are time-windowed cutsets. Within each cutset, the g-data are processed to create an n-dimensional phase-space representation of the data, described as a discrete n-dimensional vector. The method connects the flow of each phase-space point into the subsequent phase-space point, as a single connected-phase-space point, which is represented by a discrete 2n-dimensional vector. A distribution function tabulates the occurrence frequency of each discrete (connected) phase space vector for each cutset. The distribution function for a first selected cutset is compared with the distribution function for a second selected cutset whereby the differences between the dynamics for each compared cutset can be detected and measured. An output is then provided indicative of the dissimilarity.

In another aspect of the invention, one or more of the cutsets mentioned above can be used to define a basecase for the process. Using the foregoing method, the basecase cutset(s) can be used to generate a series of representative distribution functions against which all other (testcase) cutsets are compared, thus enabling an output indicative of a relative change in state or condition. The distribution function of the j-th testcase cutset can then be compared to the distribution function of each basecase cutset. The resulting measures of dissimilarity may be averaged over the basecase cutsets. When the comparison between the distribution functions of the unknown and basecase cutsets shows a significant difference, an output signal can be generated indicative of the difference or indicative of the fact of a difference. Alternatively, the base case cutset(s) can be used to establish a trend, the comparison thereafter enabling detection and/or measurement of a deviation in trend.

In another aspect of the invention there is provided apparatus comprising processing means capable of performing the method steps set forth above. The apparatus can also comprise the data sensing means or a means for receiving at least one channel of data. The apparatus also comprises an output means for providing an indication of the detection, measurement, or monitoring of the changes in condition of the process or system.

The method and apparatus according to the current invention enable a large reduction in the amount of data storage and data processing required because the distribution functions derived, and the comparison of the distribution functions, utilize only the populated states within each cutset. This improvement alone enables at least a many hundred-fold decrease in the amount of computing power required. This reduction in turn means that the method may be performed on a programmable general purpose personal computer. Alternatively, the method and apparatus may utilize a relative small amount of dedicated circuitry. Because such computers are widely available and relatively inexpensive, monitoring and analyses of data can be performed on-site and in real time.

DETAILED DESCRIPTION OF THE INVENTION

Figure 1A:
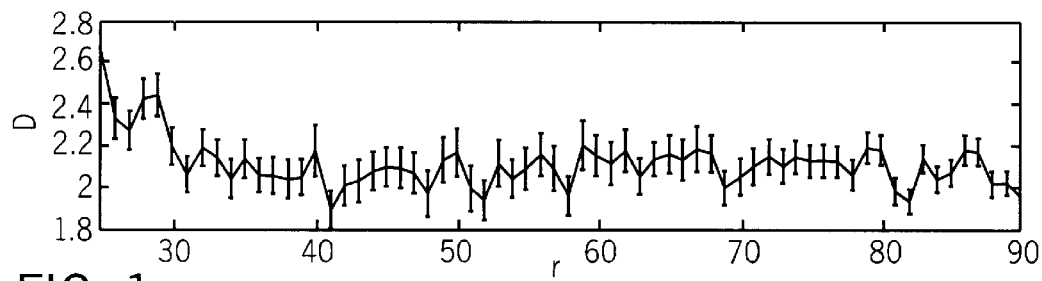
FIG. 1a is a graph of the correlation dimension (D) vs. the parameter, r, in the Lorenz attractor system.

In the following description, bracketed numbers refer to the following references, the contents of which are incorporated herein by reference:

[1] V. I. Arnold, Geometrical Methods in the Theory of Ordinary Differential Equations, Springer Publ. (1982).
[2] J.-P. Eckmann and D. Ruelle, Rev. Mod. Phys. 57, 617 (1985).
[3] H. D. I. Abarbanel, Analysis of Observed Chaotic Data, Springer Publ., New York (1996).
[4] F. Takens, Lecture Notes in Mathematics 898, 366 (1981) Springer, N.Y.
[5] T. Sauer, J. Yorke, and M. Casdagli, J. Stat. Phys. 65, 579 (1991).
[6] H. D. I. Abarbanel and M. B. Kennel, Phys. Rev. E 47, 3057 (1993).
[7] H. D. I. Abarbanel, R. Brown, J. J. Sidorowich, and L. Sh. Tsimring, Rev. Mod. Phys. 65, 1331 (1993).
[8] L. Cao, Physica D 110, 43 (1997).
[9] C. Letellier, J. Maquet, L. Le Sceller, G. Gouesbet, and L. A. Aguirre, J. Phys. A 31, 7913 (1998).
[10] A. Cover, J. Reneke, S. Lenhart, and V. Protopopescu, Math. Models and Meth. In Appl. Sciences, 7, 823–845 (1997).
[11] C. E. Shannon and W. Weaver, The Mathematical Theory of Communication, University of Illinois Press, Urbana, 1949.

[12] A. M. Fraser and H. L. Swinney, Phys. Rev. A 33,1134–1140 (1986).
[13] F. Takens, Lecture Notes in Mathematics 1125, 99–106 (1984) Springer-Verlag, Berlin.
[14] J. C. Schouten, F. Takens, and C. M. van den Bleek, Phys. Rev. E 50, 1851–1861 (1994).
[15] J. C. Schouten, F. Takens, and C. M. van den Bleek, Phys. Rev. E 49, 126–129 (1994).
[16] C. Grebogi, E. Ott, J. A. Yorke, Phys. Rev. A 37, 1711 (1988).
[17] C. Diks, W. R. van Zwet, F. Takens, and J. DeGoede, Phys. Rev. E, 53, 2169 (1996).
[18] A. M. Mood, S. A. Graybill, and D. C. Boes, Introduction to the Theory of Statistics, McGraw Hill Publ. (1974).
[19] L. M. Hively, P. C. Gailey, and V. A. Protopopescu, Phys. Lett. A, 258,103 (1999).
[20] E. N. Lorenz, J. Atmos. Sci., 30, 130 (1963).
[21] E. A. Jackson, Perspectives of Nonlinear Dynamics, vol. 2, Cambridge University Press, Cambridge, 1990.
[22] L. F. Sampine and M. K. Gordon, Computer Solution of Ordinary Differential Equations: The Initial Value Problem, Freeman Publ., 1975.
[23] T. Elbert, W. J. Ray, Z. J. Kowalik, J. E. Skinner, K. E. Graf, and N. Birbaumer, Physiol. Rev., 74, 1 (1994).
[24] R. Manuca, M. C. Casdagli, R. S. Savit, Math. Biosci., 147, 1 (1998).
[25] K. Lehnertz and C. E. Elger, Phys. Rev. Lett., 80, 5019 (1998).
[26] L. D. Iasemidis and J. C. Sackellares, Neuroscientist, 2, 118 (1996).
[27] L. M. Hively, N. E. Clapp, C. S. Daw, and W. F. Lawkins, ORNL/TM-12961 (Oak Ridge National Laboratory, Oak Ridge, Tenn.) 1995.
[28] D. F. Elliott and K. R. Rao, Fast Transforms, Analyses, Applications, Academic Press (1982).
[29] M. B. Kennel, Phys. Rev. E, 56, 316–321 (1997).
[30] L. M. Hively, in Proc. Maintenance and Reliability Conf., edited by T. E. Shannon et al. (University of Tennessee, Knoxville), 1, 16.01 (1997).
[31] L. M. Hively, V. Protopopescu, and P. C. Gailey, submitted to Chaos (2000).
[32] W. F. Lawkins, C. S. Daw, D. J. Downing, N. E. Clapp, Phys. Rev. E 47, 2520 (1993).
[33] M. Abramowitz and I. A. Stegun, Handbook of Mathematical Functions, U.S. Government Printing Office, Washington, D.C. (1964).
[34] M. Le Van Quyen, J. Martinerie, M. Baulac, and F. Varela, NeuroReport, 10, 2149 (1999).

The current invention presents a novel and robust method and apparatus for measuring condition change in nonlinear data. The invention is completely model-independent and is data driven. It can therefore be used for detecting state and/or condition changes for systems for which the dynamics are not fully understood. Indicators of condition change are defined by comparing distribution functions (DF) defined on an attractor for windowed (usually time-windowed) data sets via $L_1$ distance and $\chi 2$ statistics. The discriminating power of the new measure is shown here by testing against the Lorenz model [19]. These new measures have also been demonstrated on the Bondarenko model [31]. Also, while the method is applicable to any nonlinear data, independent of source, a specific application of the method to electroencephelogram (EEG) data is shown with the objective of capturing the transition between non-seizure and epileptic brain activity in an accurate and timely manner. The theoretical and practical results show a clear superiority of the new metrics over the traditional nonlinear measures as discriminators of condition change.

Many natural or man-made complex systems can be modeled by high dimensional systems of coupled nonlinear equations whereby the system state is represented by a time dependent vector in a high dimensional phase space (PS). Experimental investigation of the system usually deals with measuring one or a few components of this state vector. One of the main problems in the analysis of complex systems is the reconstruction of the system dynamics from scalar measurements of just one component, x. This component is generally measured at equal time intervals, although other intervals may be used. Measuring this component at equal time intervals τ beginning at time $t_0$ results in the sequence $x_j = x(t_0 + i\tau)$, i=0, 1, 2, . . . The dynamics can be represented by a d-dimensional vector, $y(i)=[x_i, x_{j+\lambda}, \ldots, x_{i+(d-1)\lambda}]$ for a system with d active variables [2] and time lag λ, with λ>τ. This PS construction captures the nonlinear relationship among time-delayed measurements of a scalar variable, while avoiding the effects of measurement imprecision [3]. The choices of lag and embedding dimension influence the nonlinear measures that can be constructed from the time series.

For noiseless data, the choice of d and λ determines how well the PS form unfolds the dynamics. Takens' embedding theorem guarantees a faithful PS reconstruction of the dynamics if the embedding space has a sufficiently high dimension d, meaning that the reconstructed trajectories do not intersect themselves and the reconstructed dynamics are smooth [4–8]. For real, that is, noisy, data the choice of d and λ is more problematic. Because real data have finite precision and are affected by noise, too high an embedding dimension may result in overfitting. Moreover, different observables of a system may contain disparate levels of dynamical information, such that PS reconstruction may be easier from one variable than from another [9].

A critical test for the method of the current invention is discrimination between different but possibly close chaotic regimes. Discriminating between regular and chaotic motion, or signaling the transition between regular and chaotic regimes is relatively straightforward [10]. Distinguishing various chaotic regimes is a difficult task, however, especially when the data are limited and/or affected by noise.

To better explain the methodology of the current invention, it is advantageous to first discuss the other nonlinear measures from time series used to show the superiority of the current invention. This will aid in understanding some of the variables used and comparisons made.

Based on the PS reconstruction, various nonlinear measures have been defined to characterize process dynamics. Three of these were chosen against which to compare the new PS metrics disclosed herein. The three are: (i) the first minimum in the mutual information function (MIF) as a measure of decorrelation time, (ii) the correlation dimension as a measure of dynamic complexity, and (iii) the Kolmogorov entropy as a measure of predictability.

The MIF is a nonlinear version of the (linear) auto-correlation and cross-correlation functions [11]. It has been applied to time series analysis [12]. The MIF measures the average information (in bits) that can be inferred from one measurement about a second measurement, and is a function of the time delay between the measurements. Univariate MIF measures predictability within the same data stream at different times. For the current analysis, the first minimum in the univariate MIF, $M_1$, was used to indicate the average time lag that makes $x_i$ independent of $x_j$. The MIF, I(Q,R), and the system entropy, H, for two measurements, Q and R, are defined by:

$$I(Q,R)=I(R,Q)=H(Q)+H(R)-H(Q,R) \quad \text{Eq. I}$$

$$H(Q)=-\Sigma P_Q(q_i)\log[P_Q(q_i)] \text{ summed over } i \quad \text{Eq. II}$$

$$H(Q,R)=-\Sigma P_{QR}(q_i, r_j)\log[P_{QR}(q_i, r_j)] \text{ summed over } i, j. \quad \text{Eq. III}$$

Q denotes one set of data measurements, $q_1, q_2, \ldots q_n$, with associated probabilities $P_Q(q_1), P_Q(q_2), \ldots, P_Q(q_n)$. R denotes a second set of data measurements, $r_1, r_2, \ldots, r_n$, with a time delay relative to the $q_i$ values, having associated probabilities $P_R(r_1), P_R(r_2), \ldots, P_R(r_n)$. The function $P_{QR}(q_i, r_j)$ denotes the joint probability of both values ($q_i, r_j$) occurring simultaneously. H and I are expressed in units of bits if the logarithm is taken in base two.

The maximum-likelihood correlation dimension, D, is defined [13, 14] by:

$$D=\{(-1/M)\Sigma\ln[(\delta_{ij}/\delta_0-\delta_n/\delta_0)/(1-\delta_n/\delta_0)]\}^{-1} \text{ summed over } i, j \quad \text{Eq. IV}$$

where M is the number of randomly sampled point pairs; $\delta_{ij}$ is the maximum-norm distance between the (randomly chosen) i-j point pairs, as defined in Eq. VI below. The distance (scale length) $\delta_n$ is associated with noise as measured from the time serial data. The distances are normalized with respect to a nominal scale length $\delta_0$, which is chosen as a balance between sensitivity to local dynamics (typically at $\delta_0 \leq 5a$) and avoidance of excessive noise (typically at $\delta_0 \geq a$). The symbol a denotes the absolute average deviation as a robust indicator of variability [14] in the time serial data:

$$a=(1/w)\Sigma|x_i-x| \text{ summed from } i=1 \text{ to } w \quad \text{Eq. V}$$

where x is the mean of $x_i$ over the window of w points. The distances $\delta ij$ are defined by:

$$\delta_{ij}=\max|x_{i+k}-x_{i+k}| \text{ the max taken } 0 \leq k \leq m-1 \quad \text{Eq. VI}$$

where m is the average number of points per cycle.

The Kolmogorov entropy, K, measures the rate of information loss per unit time or, alternatively, the degree of predictability. A positive, finite entropy generally is considered to be a clear demonstration that the time series and its underlying dynamics are chaotic. A large entropy indicates a stochastic, non-deterministic (totally unpredictable) phenomenon. The entropy is estimated from the average divergence time for pairs of initially close orbits. More precisely, the entropy is obtained from the average time for two points on an attractor to go from an initial separation ($\delta<\delta_0$) to a final separation ($\delta>\delta_0$). The maximum-likelihood entropy is calculated [15] as:

$$K=-f_s \log(1-1/b) \quad \text{Eq. VII}$$

$$b=(1/M)\Sigma b_i \text{ summed from } i=j \text{ to } M \quad \text{Eq. VIII}$$

with $b_i$ as the number of timesteps for two points, initially within $\delta<\delta_0$, to diverge to $\delta>\delta_0$. The symbol $f_s$ denotes the data sampling rate.

Entropy and correlation dimension are usually defined in the limit of zero scale length. All real data, however, have noise, and even noiseless model data are limited by the finite precision of computer arithmetic. To report the values of K and D, therefore, a finite scale length slightly larger than the noise was chosen, corresponding to a finite-scale dynamic structure. Thus, the values of K and D used here do not capture the full dynamical complexity and have smaller values than expected for the zero-scale-length limit ($\delta_0 \rightarrow 0$). To calculate these nonlinear measures, an embedding window $M_1=(d-1)\lambda$ was chosen, based on the first minimum in the MIF [12]. Then, the lag is $\lambda=\text{INT}[0.5+M_1/d-1)]$, where the function (INT) converts a decimal number to the next lower integer, and $M_1$ is measured in timesteps. For a finite sampling rate, the largest value of d for a given lag then occurs when $\lambda=\text{INT}[0.5+M_1/(d-1)] \geq 1$, or $d \leq 2M_1+1$.

Although the traditional measures defined above describe certain global features of the nonlinear dynamics, they cannot capture the host of finer details that could be responsible for condition change. The same is true for other global indicators such as fractal dimension and Lyapunov exponents. This insufficient discriminating power is due to the fact that in these indicators most dynamical details cancel each other out by averaging over many cycles. To capture the minute details, more refined indicators are needed.

The current invention provides sensitive discrimination of condition change, even in the presence of a relatively high amount of noise. For the method of the current invention, two new indicators are defined starting from the distribution function (DF), which the dynamical process defines on the attractor. The DF on the attractor is represented by discretizing each coordinate of the PS vector into S symbols, equally spaced in signal amplitude:

$$0 \leq s_i=\text{INT}[S(x_i-x_{min})/(x_{max}-x_{min})] \leq S-1. \quad \text{Eq. IX}$$

Here, $x_{min}$ and $x_{max}$ denote the minimum and maximum values of $x_i$, respectively, over the basecase data. The function INT converts a decimal number to the next lowest integer, for example, INT(3.14)=3. The DF is constructed by incrementing the population of the appropriate PS domain by one, corresponding to each vector y(i). The population in the i-th PS-DF state is denoted as $Q_i$ for the basecase and as $R_i$ for the unknown. This representation has been used for infinitely precise data [16].

Next, the DF of one cutset of data is compared to another, that is, a first selected case is compared to a second selected case. To determine changes in state, the DF of an unknown (testcase) process state is compared to that of a basecase. Previous work [17] measured distances between delay vector distributions by the square of the distance between two DFs. Here the difference between $Q_i$ and $R_i$ is measured by $\chi^2$ statistics and $L_i$ distance:

$$\chi^2=\Sigma(Q_i-R_i)^2/(Q_i+R_i) \text{ summed over } i \quad \text{Eq. X}$$

$$L=\Sigma|(Q_i-R_i)| \text{ summed over } i \quad \text{Eq. XI}$$

where the summations in both equations run over all of the populated PS states. The $\chi^2$ statistics is one of the most powerful, robust, and widely-used statistical tests to measure discrepancies between observed and expected frequencies. The $L_1$ distance is the natural metric for DFs because it is directly related to the total invariant measure on the attractor. To apply these measures properly, the total population of the unknown DF must be scaled (summed over all the domain populations in $R_i$) to be the same as the total population of the basecase. The sum in the denominator of Eq. X is based on a test for equality of two multinomial distributions [18].

Connecting successive PS points as indicated by the dynamics $y(i) \rightarrow y(i+1)$ provides a discrete representation of the process flow [3]. This approach enables the extension of the PS method to capture even more dynamical information using pair-wise connectivity between successive d-dimensional PS states, thus forming a 2d-dimensional vector Y(i)=[y(i), y(i+1)] in the connected-PS (CPS). The connected distribution functions (CDF) are $Q_{ij}$ and $R_{ij}$ for the basecase and the unknown processes, respectively. The index i denotes the beginning (i-th) PS state and j denotes the subsequent (j-th) PS state. The connected $\chi^2$ statistic, $\chi_c^2$, and the connected $L_1$ distance, $L_c$, are defined as above:

$$\chi_c^2 = \Sigma(Q_{ij} - R_{ij})^2 / (Q_{ij} + R_{ij}) \text{ summed over } ij \quad \text{Eq. XII}$$

$$L_c = \Sigma(Q_{ij} - R_{ij}) \text{ summed over } ij \quad \text{Eq. XIII}$$

where the subscript (c) indicates the CDF measure.

The measures defined in Eqs. X–XIII satisfy the following inequalities:

$$\chi^2 \leq L \quad \text{Eq. XIV}$$

$$\chi_c^2 \leq L_c \quad \text{Eq. XV}$$

$$L \leq L_c \quad \text{Eq. XVI}$$

$$\chi^2 \leq \chi_c^2 \quad \text{Eq. XVII}$$

These inequalities have been rigorously proven and verified numerically [19]. They indicate that (i) the $L_1$ distance is more discriminating than the $\chi^2$ statistic and (ii) the connected PS measures contain more information, and therefore are more discriminating, than the corresponding non-connected PS measures.

In the application of the new PS measures to discriminate condition change, the DF values depend on one another due to the PS construction from time delay vectors with dynamical structure [17]. The resulting statistical bias is avoidable by averaging contributions to Equations X and XII over values of y(j) or Y(j) that satisfy $|i-j|<\Lambda$[17], where $\Lambda$ is some largest typical correlation scale length in the time series. The bias in a typical sample was tested by sampling every $\Lambda$-th CPS point for $4 \leq \Lambda \leq 23$, resulting in $\Lambda$ different samples for the base case ($Q_i$) and for each cutset ($R_i$). The sampled $\chi^2$ values were averaged over the $\Lambda^2$ different combinations of DFs for the basecase and the testcase cutsets. As expected, a decrease proportional to $1/\Lambda$ occurs in the sampled $\chi^2$ values because the number of data points contributing to $\chi^2$ decreases in the same proportion. The trend over time in sampled $\chi^2$ values remains the same as in $\chi^2$ values without sampling, showing that no unexpected bias is present. Thus, the unsampled $\chi^2$ values are used in the examples herein as a relative measure, rather than as an unbiased statistic for accepting or rejecting a null statistical hypothesis.

Other aspects of the invention can be mentioned here, although they are incorporated by reference as pointed out above, and are a part hereof, and are explained in the following examples. One of these aspects is the zero-phase quadratic filter applied to the data. The filter involves fitting the data to a quadratic equation with the result that unwanted artifacts in the data are removed. The fitting takes place over a window, the length of which can be determined by those of skill in the art and/or by preprocessing the data. Typically, the windows are selected to overlap. The preferred filter is fully disclosed in U.S. Pat. No. 5,626,145, already incorporated herein by reference.

Also, a renormalization technique can be incorporated in the steps of the method. A preferred method of renormalization is set forth below, which differs from other known methods. Renormalizing the results obtained from the comparison of one DF to another presents the data in a framework that facilitates comparison. By facilitating comparison, the method and/or use of the apparatus is accessible to a wide range of users, rather than only to those of high skill in the relevant art. In particular, the disparate range and variability of the various nonlinear measures are difficult to interpret, so this invention uses a renormalized form as a consistent means of comparison. For each nonlinear measure, V, we define $V_i$ as the average value of nonlinear measure for the i-th cutset. To demonstrate renormalization for this invention, V can be any of the measures in the set {L, $L_c$, $\chi^2$, $\chi_c^2$, D, K, and $M_1$}, where the first four are the dissimilarity metrics as defined above, $M_1$ is the first minimum in the mutual information function [11–12], D is the correlation dimension [13–14], and K is the Kolmogorov entropy [15]. The symbol $\overline{V}$ denotes the mean value of that nonlinear measure over the non-outlier basecases (described below), with a corresponding sample standard deviation, $\sigma$. The renormalized form is then $U(V) = |V_i - \overline{V}|/\sigma$, which measures the number of standard deviations that the testcase deviates from the basecase mean. For a positive indication of change, we use a threshold, $U > U_c = 3.09$, corresponding to a false positive probability of $<10^{-3}$ in Gaussian random data. We require two or more consecutive occurrences of a positive indication to avoid spurious false positives, corresponding to ajoint false positive probability of $<10^{-6}$ in Gaussian data.

The discriminating power of the new measures has been demonstrated for the Lorenz [19, 20] (detailed below) and Bondarenko [31] models. The Bondarenko model [31] is interesting for simulation of brain activity that resembles actual EEG. As stated before, traditional nonlinear measures provide reasonably good indicators of a bifurcation or transition to chaos. Transitions between two chaotic regimes are not readily detected by traditional nonlinear measures, however, especially for relatively small changes in the parameter that underlies the transition. The nonlinear phase-space measures of this invention do readily detect such chaotic transitions, and have consistently outperformed the traditional nonlinear measures in detecting condition change [23–26].

EXAMPLE 1

Testing on the Lorenz Model

The discriminating power of the new measures was assessed by testing on the well-known Lorenz model [20]:

$$dx/dt = a(y-x) \quad \text{Eq. XVIII}$$

$$dy/dt = rx - y - xz$$

$$dz/dt = xy - bz.$$

As stated before, some traditional nonlinear measures are good indicators of a bifurcation or transition to chaos. However, transitions between two chaotic regimes are not readily detected by these measures, especially for relatively small changes in the parameter that underlies the transition. The current work therefore concentrates on detecting non-stationarity within a region where the Lorenz system is known to behave chaotically [21]: a=10, b=8/3, and $25 \leq r \leq 90$.

The model is integrated using a multistep, multi-order method [22]. The geometric size of the Lorenz attractor increases by almost four-fold as r increases from 25 to 90. Thus, a fixed value of time step size spans more distance on the attractor as r increases, causing the loss of important dynamical detail at larger values of r. Accordingly, the size of the time step $\tau$ is decreased in inverse proportion to r, $\tau = 0.025(25/r)$ and the number of cutset data points w is increased in proportion to r, $w = 80000(r/25)$. This provides roughly the same amount of geometrical (dynamical) detail within one time step over all values of r, while also capturing the same amount of information about the cyclic motion on the attractor. Because the size of the Lorenz attractor is known in this instance, the scale can be accordingly adjusted. However, even for complex systems with no known model (e.g., brain waves), the size of the phase space can be known by preprocessing the data and proceeding in a similar fashion.

Figure 1B:
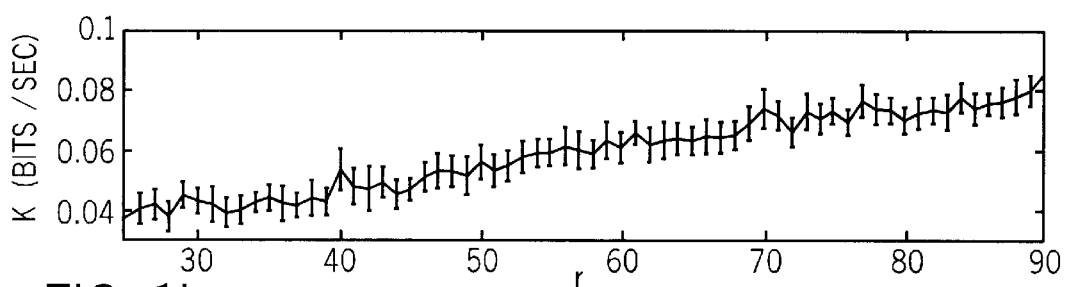
FIG. 1b is a graph of the Kolgomorov entropy, K, vs. the parameter, r, in the Lorenz attractor system.
Figure 1C:
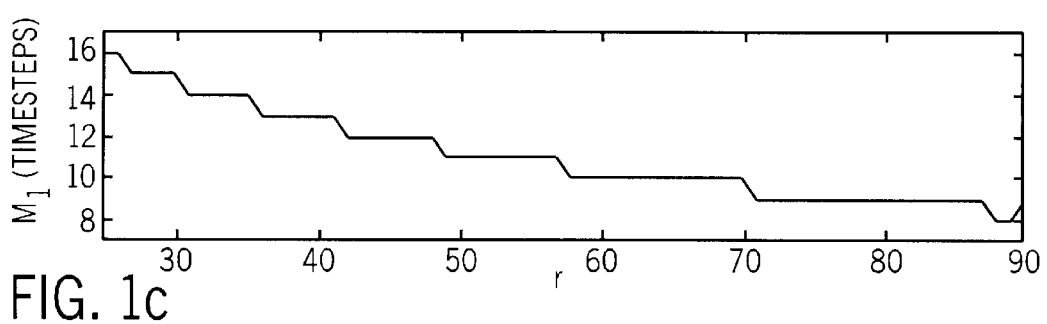
FIG. 1c is a graph of the first minimum in the mutual information function, $M_1$, vs. the parameter, r, in the Lorenz attractor system.
Figure 1D:
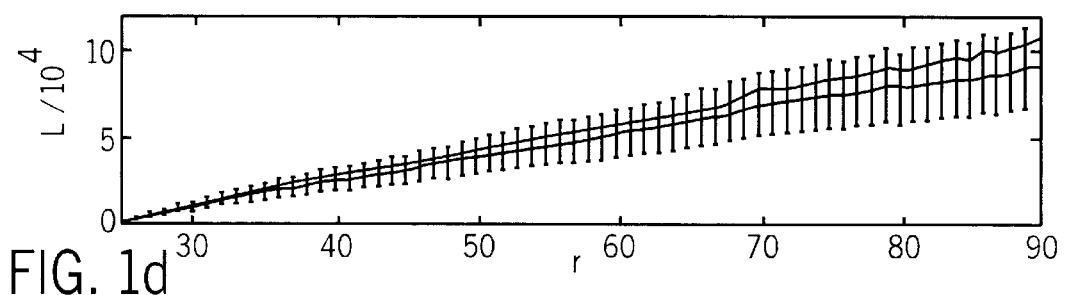
FIG. 1d is a graph of the dissimilarity measure $\chi 2/10^5$ vs. the parameter, r, in the Lorenz attractor system.
Figure 1E:
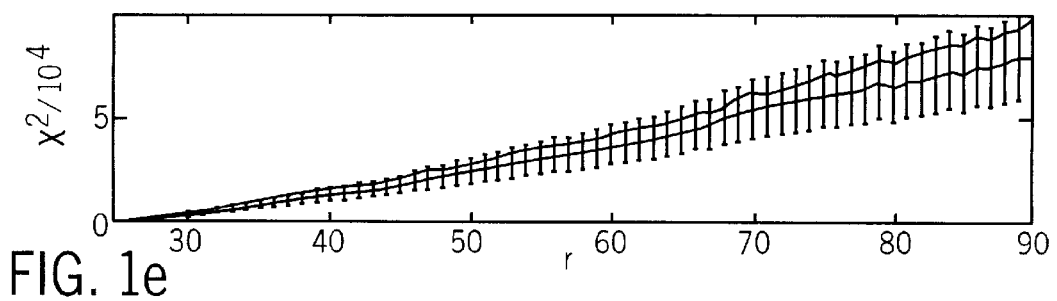
FIG. 1e is a graph of the dissimilarity measure $L/10^5$ vs. the parameter, r, in the Lorenz attractor system.

FIG. 1 shows various nonlinear measures versus r, by analyzing only the time serial values of z. The correlation dimension (FIG. 1a) varies erratically between 1.7 to 2.15 over the whole range of r. The Kolmogorov entropy (FIG. 1b) also varies irregularly between 0.03 to 0.05. FIG. 1c shows the location of $M_1$, with a monotonic but step-wise increase as r rises, so that relatively large variations in r are poorly indicated (e.g., for $60 \leq r \leq 72$). A reduction in integration step size would reduce the size of these step-wise regions, but this example serves as a realistic test of these measures on real data with a limited sampling rate when such reduction is not possible. In sharp contrast, the PS and CPS measures increase almost monotonically from zero to $>10^5$ as r rises from 25 to 90. The values of L and $\chi^2$ essentially coincide over the whole range because the measures are dominated by (C)PS domains that are populated only for the basecase ($Q_i > 0$ for $R_i = 0$) and only for the unknown ($R_i > 0$ for $Q_i = 0$), for which the two measures become analytically equivalent. The (C)PS measures are obtained by partitioning each Lorenz data set into four non-overlapping cutsets of equal length, with the basecase corresponding to r=25. Each of the four testcase cutsets is compared to each of the four basecase cutsets, yielding sixteen values for each of the four change metrics, which FIGS. 1d and 1e show as corresponding averages and error bars (standard deviations of the means). Error bars are shown for the PS metrics only, because error bars for the CPS curves overlap therewith, producing unnecessary clutter. As expected from Eqs. XIV–XVII, the CPS measures are stronger than their non-connected PS counterparts.

EXAMPLE 2
Application to Bondarenko Model

The phase-space measures were also assessed by testing them on the Bondarenko neuron model [31], which is a coupled set of time-delayed ordinary differential equations:

$$du_i/dt = -u_i(t) + \sum_{j=1}^{M} a_{ij} f(u_j(t - \tau_j))$$ Eq. XIX

The signal from the i-th neuron is $u_i(t)$. The indices, i and j, run from 1 to M=10 for ten neurons. The matrix, $a_{ij}$, is a set of coupling coefficients having uniformly random values, $-2 \leq a_{ij} \leq 2$. The time delay is a constant, $\tau_j = 10$. The function, f(x)=c tanh(x), simulates nonlinear neural response to signals from neighboring neurons. Dissimilarity was measured within a region where the Bondarenko system is known to behave chaotically: $5 \leq c \leq 16$. The model was integrated using a standard fourth-order Runge-Kutta method with a timestep of h=0.3. A time of $4 \times 10^8$ h was allowed for the solution to achieve stationarity after initiating the integration with random impulses, $u_i(t=0)=\rho_i$ with $\rho_j$ having uniformly random values, $-2 \leq \rho_j \leq 2$. One hundred thousand (100,000) data values of $u_i$ at fixed time intervals of $\Delta t=60$ were calculated for each value of c. The (connected) phase space measures were obtained by partitioning each 100,000-point Bondarenko dataset into four non-overlapping subsets of 25,000 points each, for comparison to each of the 25,000-point subsets of basecase at c=5. Each of the four testcase subsets were compared to each of the four basecase subsets, yielding sixteen values for each of the four measures of dissimilarity, from which were obtained a mean and the standard deviation of the mean. One of the ten neuron signals was used for dissimilarity detection. The correlation dimension varies. erratically between 3.5 and 8.5 as c increases from 5 to 16. Over the same range of c, the Kolmogorov entropy rises almost monotonically from 0.025 to 0.16. The location of the first minimum in the mutual information function, $M_1$, also varies erratically as c increases. In sharp contrast, the (connected) phase space measures increase almost monotonically from zero to more than $8 \times 10^4$ as c rises from 5 to 16. The values of L and $\chi^2$ essentially coincide over the whole range because the measures are dominated by phase space bins that are populated only for the basecase $P_i > 0$ for $Q_i = 0$ and only the testcase $P_i > 0$ for $Q_i = 0$, for which the two measures become analytically equivalent.

EXAMPLE 3
Application to EEG Data

The invention has been demonstrated using sixteen-channel, analog scalp data in the bipolar montage from archival VHS tapes [27]. Only one channel (channel 13, closest to the patient's right eye) is used. This data is digitized at a sampling rate of 512 Hz with 12-bit precision, corresponding to integers between –2,048 and +2,047. Table 1 summarizes these nine datasets with monitoring periods of 1,380–3,115 seconds, and with the clinical seizure beginning at times that range over 966–2,775 seconds.

The invention has also been applied to digital EEG scalp data from other clinical sites in the 10/20 International System of electrode placement, sampled at 200 Hz. These data have 10–11 bits of precision, with signal amplitudes between 0–3,000 depending on the dataset. These data have 23–32 channels with monitoring periods of 2,217–20,000 seconds. The clinical seizures begin at times that range over 1,930–15,750 seconds. Only one clinically designated channel was examined in each of these eleven datasets, as shown in Table 1.

TABLE 1

Summary of EEG data

| Dataset # | # Channels | Seizure (s) | Tot Time (s) | Channel | Sample Rate (Hz) |
|---|---|---|---|---|---|
| 109310 | 16 | 2775 | 3115.3 | 13 | 512 |
| 109314 | 16 | 2480 | 2742.4 | 13 | 512 |
| 119230 | 16 | 2491 | 2917.4 | 13 | 512 |
| 119234 | 16 | 2560 | 2649.6 | 13 | 512 |
| 62723t | 16 | 2620 | 3060.8 | 13 | 512 |
| 69212 | 16 | 2356 | 2547.8 | 13 | 512 |
| 73305d | 16 | 1245 | 1380 | 13 | 512 |
| c8492d | 16 | 966 | 1603.6 | 13 | 512 |
| wm12sd | 16 | 1041 | 1428.6 | 13 | 512 |
| szpr00 | 23 | 5236 | 5401 | Fp2 | 200 |
| szprec | 32 | 1930 | 2217 | F7 | 200 |
| szpr03 | 32 | 1932 | 2217 | T4 | 200 |
| szpr04 | 23 | 3794 | 3963 | T4 | 200 |
| ezpr05 | 23 | 4888 | 6000.2 | T4 | 200 |
| emu02 | 27 | 4320 | 15,006 | F4 | 200 |
| emu03 | 27 | 13,200 | 16,228 | C3 | 200 |
| emu04 | 27 | 15,750 | 18,423 | C4 | 200 |
| emu14 | 27 | 4080 | 20,000.2 | F4 | 200 |
| emu18 | 27 | 4200 | 18,000.2 | T3 | 200 |
| emu26 | 27 | 13,987 | 16,224 | Fp1 | 200 |

All scalp EEG are obscured by muscular activity due to eye blinks, facial twitches, etc. These artifacts are avoidable by obtaining EEG data from depth or subdural electrodes, but such methods are invasive and non-ambulatory. By use of the method according to the current invention, such invasive and possibly dangerous procedures are avoided. Moreover, a patient being monitored using the method and apparatus of the current invention is not rendered non-ambulatory. Artifacts such as those caused by musculature activity were not removed via standard linear filtering techniques, which add unacceptable phase distortions to the filtered data [32]. Instead, most of the low frequency artifacts were removed from the scalp EEG with a novel zero-phase quadratic filter ("Method And Apparatus For Extraction Of Low-Frequency Artifacts From Brain Waves For Alertness Detection," U.S. Pat. No. 5,626,145), thereby retaining the nonlinear amplitude and phase relationships [27]. This filter uses a moving time window of 2n+1 points of raw EEG data, $e_i$, with the same number of data samples, n, on either side of a central point. The artifact signal, $f_i$, is estimated at the central point from a quadratic regression over the 2n+1 points. The artifact filtered signal, $g_i$, is then $g_i=e_i-f_i$. The filter window width corresponds to eye blink activity at £2 Hz, for which n=128 in the nine datasets with a 512 Hz sampling rate, and n=50 in the eleven datasets with a 200 Hz sampling rate. All subsequent EEG analysis uses this artifact-filtered data. N=22,000 data points (43 s) were chosen for each cutset of the nine datasets, sampled at 512 Hz. This value balances the improvement in forewarning time discrimination at smaller N, with the statistical power to measure dissimilarity at larger N. For this same reason, N=22,000 data points (110 s) were chosen for each cutset of the eleven datasets, sampled at 200 Hz.

Our previous analysis of EEG data [27, 30] found correlation dimension values of 1–2.6 for non- and pre-seizure activity, and $\leq 6$ during a seizure, consistent with others' work [23, 25]. These results suggest a choice of $d \leq 7$ for the connected phase space reconstruction. It is found, however, that d=7 overfits the EEG data due to noise, modest cutset size, and the finite precision. For this work, each phase-space construction parameter was iteratively varied, with the others fixed, to obtain optimum sensitivity of the phase-space measures to EEG changes. All EEG analyses were subsequently performed with the single best choice for S, d, and N. We find that values of d=3 and S=22 provide the best sensitivity to condition change for this work. The value of $M_1$ is taken from the first 430 seconds of (non-seizure) data in the nine datasets, sampled at 512 Hz. The value of $M_1$ is taken from the first 1,100 seconds of data in the eleven datasets, sampled at 200 Hz.

The first ten non-overlapping cutsets in each of the datasets were used as basecases. This choice is a balance between a reasonably short basecase period to capture quasi-stationary non-seizure activity and a sufficiently long period for statistical significance. However, a few of these basecases are very different from typical non-seizure activity, causing a severe bias in the detection of condition change. Thus, the data is statistically tested for outlier cutsets as follows. Comparisons among the ten basecase cutsets yields forty-five (=9×10/2) unique pairs, from which is obtained an average, V, and sample standard deviation, σ, for each of the dissimilarity measures, V={L, $L_c$, $\chi^2$, and $\chi_c^2$}. A chi-squared statistic, $\Sigma(V_{ij}-V)^2/\sigma^2$, is calculated for each of these four dissimilarity measures. The index j is fixed, and the sum is over i≠j, for comparison of the j-th basecase to the other nine, non-overlapping basecase cutsets, giving nine degrees of freedom. The null statistical hypothesis allows a random outlier in these forty-five unique comparisons with a probability of <1/45, corresponding to less than one out of the forty-five unique pairs. Thus, an outlier cutset is identified as having the largest chi-squared statistic over the four dissimilarity measures >19.38, corresponding to a random probability of >1/45. If this analysis does not identify any outlier, then the previous values of V and σ are used for subsequent renormalization, as described below. If this analysis identifies an outlier, it is removed and this analysis is repeated for the remaining nine basecase cutsets. Repeated application of this analysis identifies any additional outliers when the largest chi-squared statistic exceeds the below threshold, corresponding to a probability greater than 2/B(B-1), as interpolated from standard statistical tables for (B-1) degrees of freedom [33]. Here, B is the number of non-outlier basecase cutsets.

| B | chi-squared threshold |
|---|---|
| 10 | 19.38 |
| 9 | 17.24 |
| 8 | 15.03 |
| 7 | 12.74 |
| 6 | 10.33 |

This approach dramatically improves the robustness of the condition change detection. If the analysis identifies five (or more) outliers, all ten basecases must be rejected as unrepresentative, and a new set often cutsets as basecases acquired. The current analysis, however, never finds more than four outliers. Subsequently, the non-outlier basecase cutsets are compared to each non-overlapping testcase cutset, and average values obtained for the dissimilarity measures for each testcase.

The disparate range and variability of the various nonlinear measures are difficult to interpret, so a consistent means of comparison is needed. Thus, the nonlinear measures are converted to a renormalized form [19, 31]. For each nonlinear measure, V={D, K, $M_1$, L, $L_c$, $\chi^2$, and $\chi_c^2$}, $V_i$ is defined as the average value of nonlinear measure for the i-th cutset. As before, V is the mean value of the nonlinear measure over the non-outlier basecases, with a corresponding sample standard deviation, σ, as described above. The renormalized form is then $U(V)=|V_i-V|/\sigma$, which measures the number of standard deviations that the testcase deviates from the basecase mean. For a positive indication of change, $U>U_c=3.09$ is used, corresponding to a false positive probability of $<10^{-3}$ in Gaussian random data. Two or more consecutive occurrences of a positive indication are set as the requirement to avoid spurious false positives, corresponding to a joint false positive probability of $<10^{-6}$ in Gaussian data. These renormalized forms are used for measuring changes in EEG.

Figure 2A:
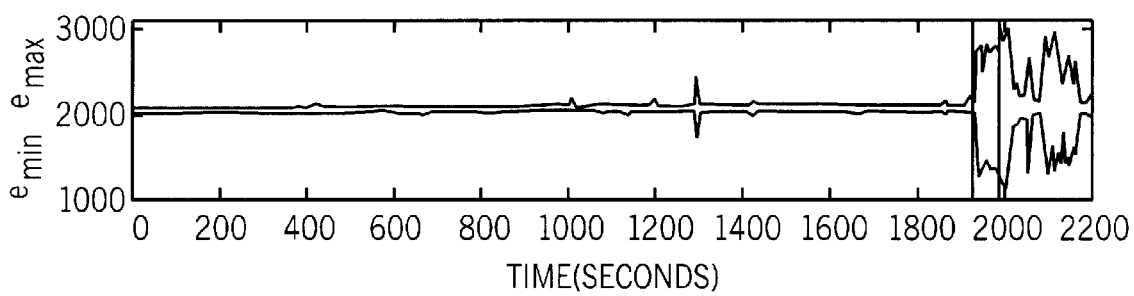
FIG. 2a is a graph of the $e_{min}$ and $e_{max}$ in raw EEG data vs. time.
Figure 2B:
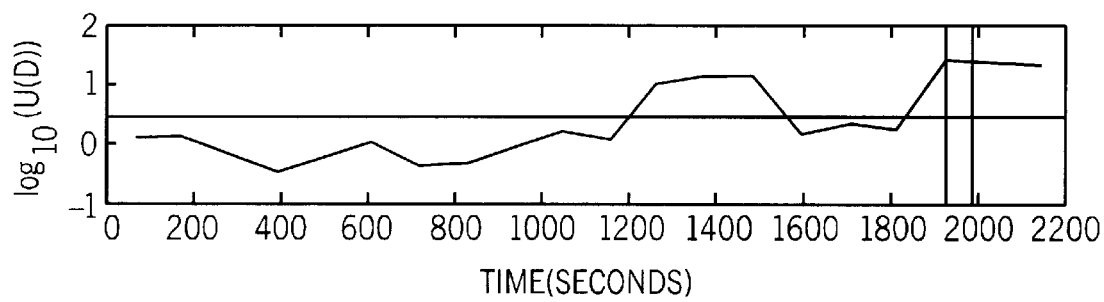
FIG. 2b is a graph of the $\log_{10}$ of the correlation dimension (D) vs. time for a sample time dependent dataset.
Figure 2C:
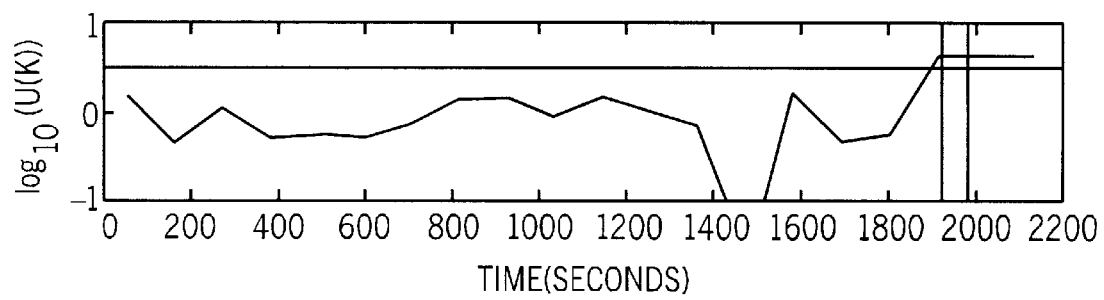
FIG. 2c is a graph of the $\log_{10}$ of the Kolgomorov entropy, K, vs. time for a sample time dependent dataset.
Figure 2D:
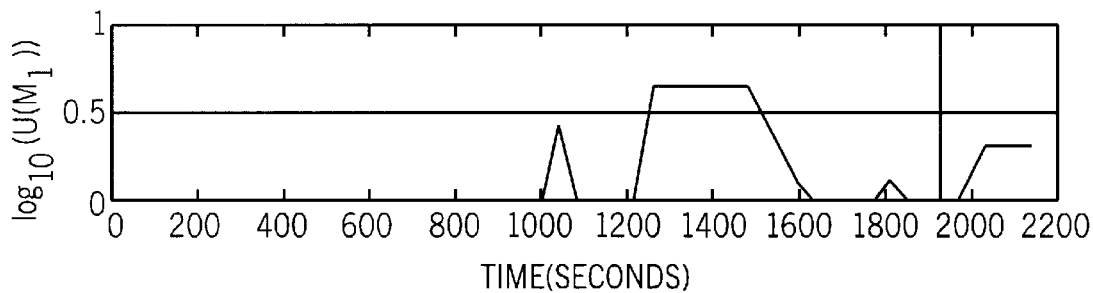
FIG. 2d is a graph of the $\log_{10}$ of first minimum in the mutual information function, $M_1$, vs. time in the Lorenz model for a sample time dependent dataset.
Figure 2E:
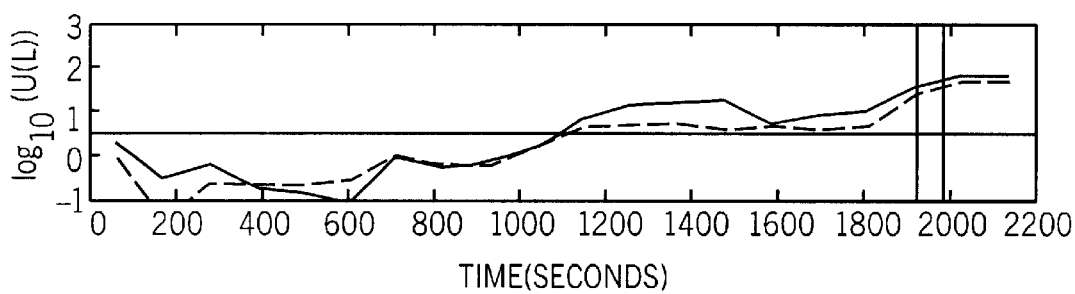
FIG. 2e is a graph of the $\log_{10}$ of the dissimilarity measure $\chi 2$ vs. time for a sample time dependent dataset.
Figure 2F:
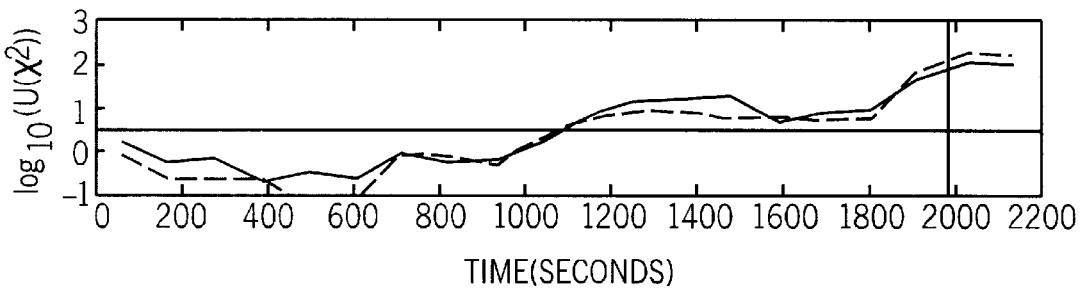
FIG. 2f is a graph of the $\log_{10}$ of the dissimilarity measure L vs. time for a sample time dependent dataset.

FIG. 2 shows the renormalized nonlinear measures for an example dataset #szprec. The vertical lines in these plots indicate onset of the clinical seizure at 1,930 seconds and subsequent post-seizure period. The nonlinear measures are plotted at the center of the time window for each cutset. All of the measures show low to modest variability during the period of nonseizure brain activity (<900 seconds). FIG. 2a shows the minimum, $e_{min}$, and maximum, $e_{max}$, in the raw EEG signal with no clear pre-seizure features in the signal envelop. Other subplots (FIGS. 2b–2f) show the renormalized nonlinear measures, with a horizontal line indicating the threshold for condition change detection, $U_c=3.09$. Correlation dimension, D (FIG. 2b) rises above the threshold from 1,250–1,500 seconds, subsequently falls below the threshold, and then rises above threshold at 1,925 seconds through the seizure. Kolmogorov entropy, K (FIG. 2c) provides no preseizure indication, and rises above $U_c$ only during the seizure. The first minimum in the mutual information function, $M_1$ (FIG. 2d) exceeds $U_c$ from 1,250–1,500 seconds, then falls below the threshold without any seizure indication. In sharp contrast to these weak pre-seizure indications, the renormalized phase-space measures (FIGS. 2e–2f) all rise above the threshold at 1,155 seconds, rising still further near and immediately following the seizure.

forewarnings of more than one hour (datasets #emu003, emu004, emu026) are too long to be clinically useful. The data more than adequately support the conclusion that the phase space measures are much superior to the conventional nonlinear measures as preseizure indicators of condition change for a single channel of scalp EEG.

TABLE 2

Times (seconds prior to seizure) when change is detected

| Dataset # | D | K | $M_1$ | $L_c$ | L | $\chi_c^2$ | $\chi^2$ |
|---|---|---|---|---|---|---|---|
| 109310 | 1099 | * | * | −61 | −61 | 1142 | −61 |
| 109314 | 1921 | 1406 | 1835 | 1878 | 1921 | 1921 | 1921 |
| 119230 | 901 | 386 | −216 | 471 | −44 | 471 | 514 |
| 119234 | 1915 | * | * | 1915 | 1915 | 1915 | 1915 |
| 62723t | 1374 | * | −44 | 2233 | 1675 | 2233 | 2233 |
| 69212 | * | 165 | 637 | 1626 | 1497 | 1626 | 1626 |
| 73305d | 600 | 600 | * | 343 | 772 | −87 | 772 |
| c8492d | −22 | 321 | 364 | 193 | 193 | 193 | 193 |
| wm12sd | * | * | * | −76 | 10 | 10 | 10 |
| szprec | 500 | −160 | 500 | 610 | 610 | 610 | 610 |
| szpr00 | * | * | 1496 | 726 | −154 | 836 | 1716 |
| szpr03 | −158 | −158 | 172 | 502 | 502 | 502 | 502 |
| szpr04 | −166 | * | −166 | 384 | 384 | 384 | 384 |
| szpr05 | 3568 | 3348 | 3568 | 3678 | 3568 | 3678 | 3568 |
| emu002 | * | −190 | −410 | 2230 | 2780 | 1900 | 2780 |
| emu003 | * | * | * | 12760 | 12760 | 12760 | 12760 |
| emu004 | * | 6950 | * | 13660 | 13550 | 14540 | 13660 |
| emu014 | * | * | −540 | 670 | 670 | −210 | 670 |
| emu018 | −90 | −1630 | −310 | 3650 | 2220 | 3650 | 2220 |
| emu026 | 11127 | 11237 | 4747 | 11237 | 11237 | 11237 | 11237 |

Entries with an asterisk * show no positive indication of change.
For each dataset, bold entries denote the earliest time of change.

Figure 3A:
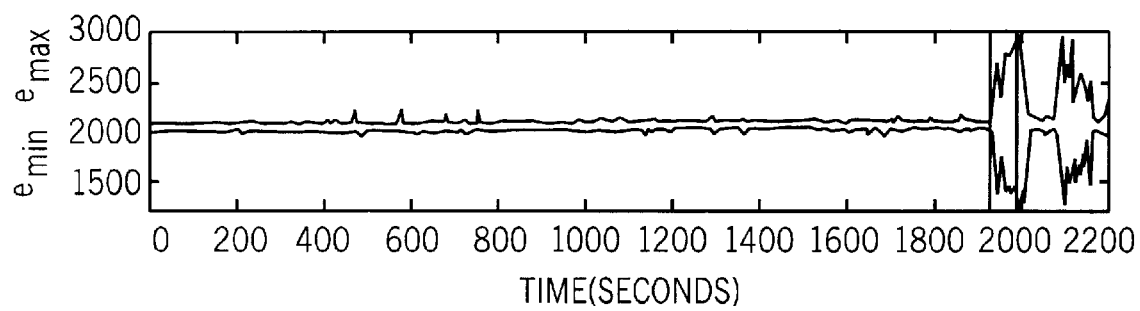
FIG. 3a is a graph of the $e_{min}$ and $e_{max}$ in raw EEG data vs. time for a second dataset.
Figure 3B:
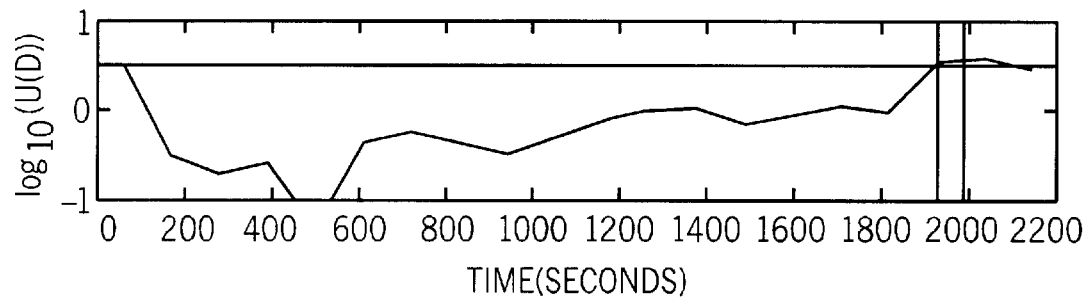
FIG. 3b is a graph of the $\log_{10}$ of the renormalized correlation dimension (D) vs. time for a second time dependent dataset.
Figure 3C:
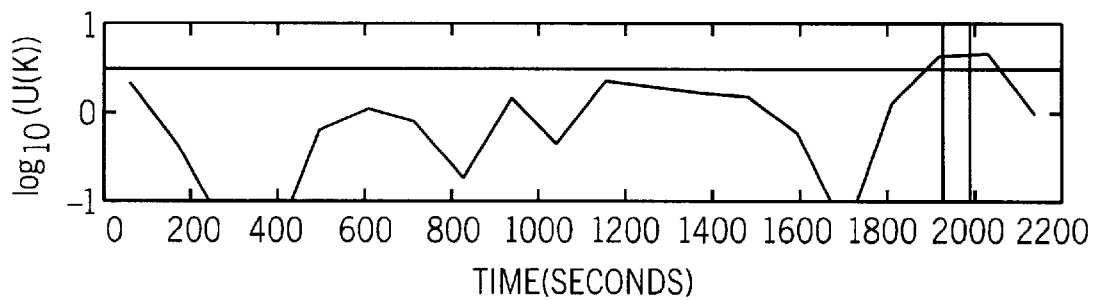
FIG. 3c is a graph of the $\log_{10}$ of the renormalized Kolgomorov entropy, K, vs. time for a second time dependent dataset.
Figure 3D:
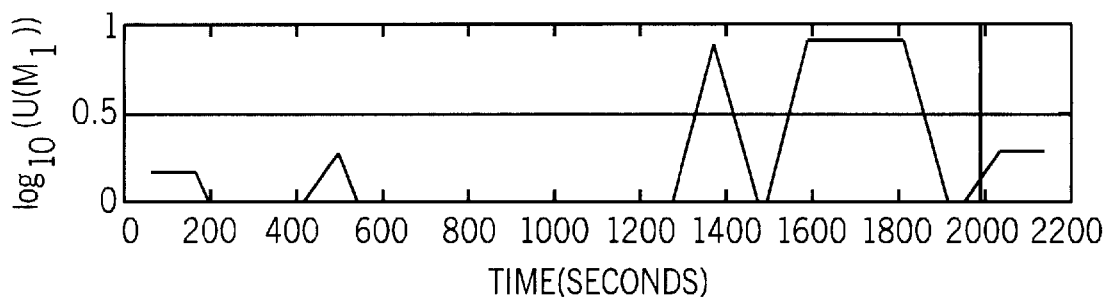
FIG. 3d is a graph of the $\log_{10}$ of the renormalized first minimum in the mutual information function, $M_1$, vs. time for a second time dependent dataset.
Figure 3E:
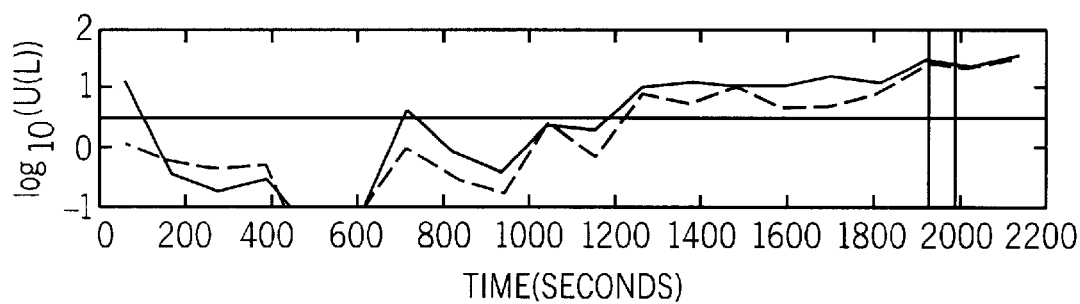
FIG. 3e is a graph of the $\log_{10}$ of a renormalized dissimilarity measure $\chi 2$ vs. time for a second time dependent dataset.
Figure 3F:
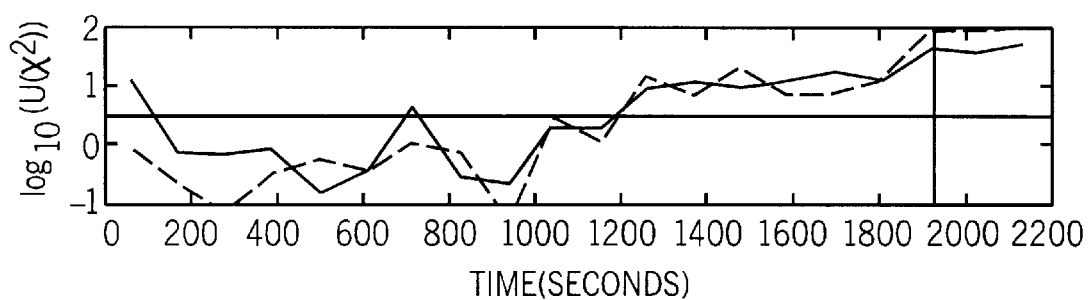
FIG. 3f is a graph of the $\log_{10}$ of a renormalized dissimilarity measure L vs. time for a second time dependent dataset.
Figure 4:
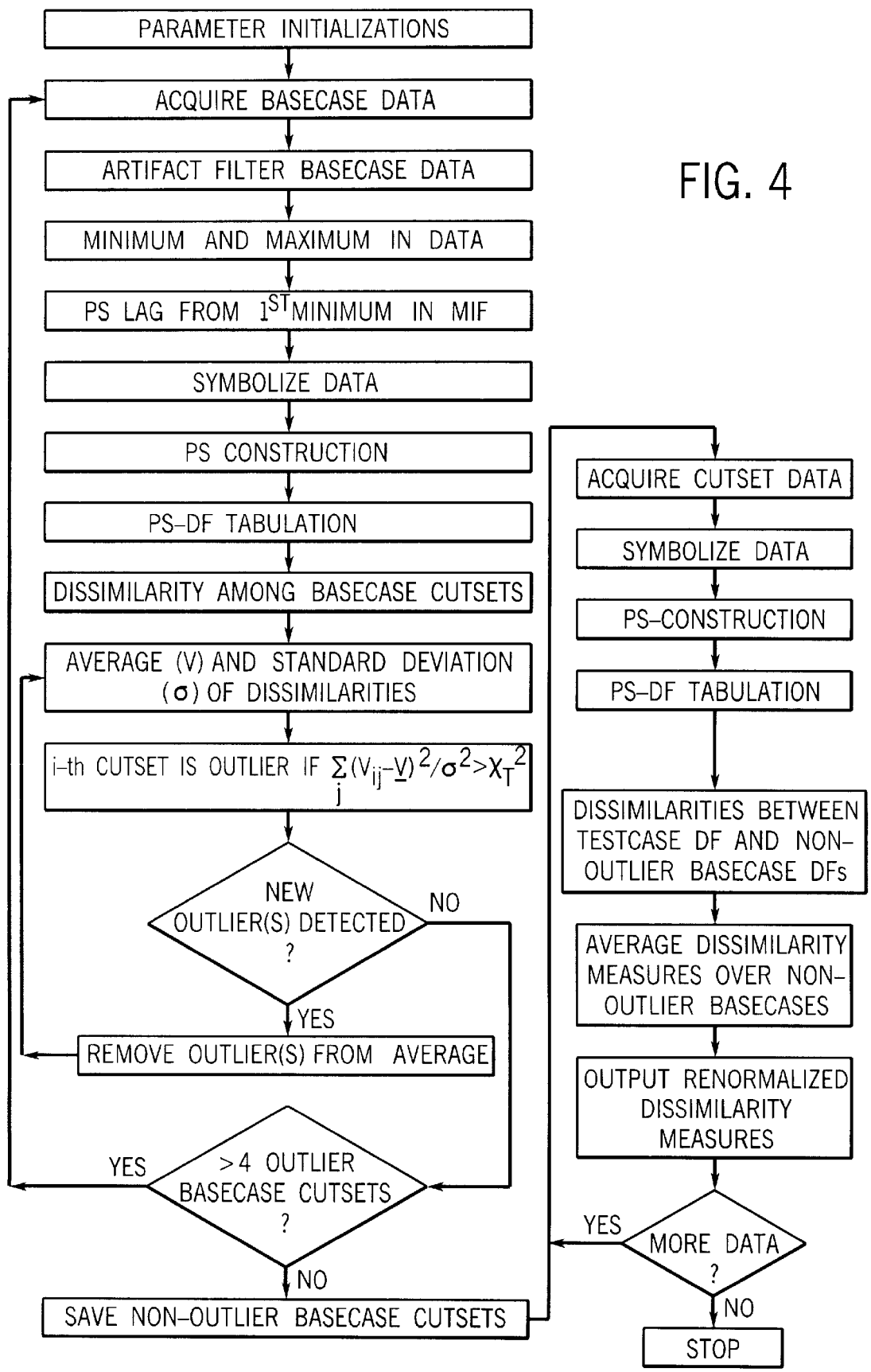
FIG. 4 is a flow chart of the sequence of acts in the method of the present invention.

FIG. 3 displays the renormalized nonlinear measures for another sample dataset #szpr03, for which the onset of clinical seizure occurs at 1,932 seconds. FIG. 3a shows the minimum, $e_{min}$, and maximum, $e_{max}$, in the raw EEG signal with little preseizure amplitude variability, except four positive spikes between 450–750 seconds. D (FIG. 3b) and K (FIG. 3c) give essentially no preseizure warning, exceeding the threshold for condition change immediately prior to and during the seizure. $M_1$ exceeds $U_c$ at 1,375 seconds and at 1,595–1,815 seconds (FIG. 3d), but does not indicate the seizure. The connected phase-space measures (solid lines in FIGS. 3e–3f) show a single excursion above threshold at 715 seconds. Subsequently, all of the phase-space measures rise and stay above $U_c$, beginning at 1,265 seconds through seizure.

Table 2 summarizes the forewarning times for each measure over twenty sample EEG datasets. A negative value of forewarning time corresponds to an indication after seizure onset. Starred (*) values indicate that no condition change was detected by this measure. Analysis of normal EEG shows no positive indication of change. These results were assessed as follows. The phase space measures provide the earliest seizure forewarning in 11, 10, 14, and 13 datasets for L, $L_c$, $\chi_c^2$, and $\chi^2$, respectively. Moreover, the phase-space measures provide preseizure indications in all twenty cases. In sharp contrast, the traditional nonlinear measures only give the earliest forewarning of a seizure in 1, 1, and 3 instances for K, $M_1$, and D, respectively. These same traditional measures provide no forewarning of a seizure in 7, 8, and 6 cases, respectively. The sum of the earliest-forewarning times exceeds twenty, because more than one measure can simultaneously detect condition change. It is noted that the forewarning time (10 seconds) for dataset #wm12sd is too short to be clinically useful. In addition, the The current invention differs markedly from previous work [25, 26, 34]:

First, previous investigations used data from multichannel data from subdural and depth electrodes, while the method of this invention uses only one channel of scalp EEG data that allows non-invasive, ambulatory, long-term, non-clinical monitoring. In the context of other types of nonlinear systems, this demonstrates that discriminating between similar but different states can be accomplished with less data, and with data that is more easily acquired.

Second, prior effort used invasive monitoring to avoid low-frequency artifacts, which are removed from scalp data with a novel zero-phase quadratic filter to improve the data quality. Thus the method of the current invention enables discrimination with data of lesser quality, that is, even in the presence of relatively high noise levels in the data.

Third, previous investigations focused only on temporal lobe epilepsy. It has been earlier determined that there are no consistent trends in conventional nonlinear measures for various seizure types. The current invention demonstrates the successful use of new measures of condition changes for any seizure. The invention thus has broad applicability to nonlinear systems. The new level of analyses provided by the invention enables the monitoring and comparison of hitherto known but indistinguishable states in systems, and provides a practical tool for the detection, monitoring, and discrimination between hitherto unknown or undetectable states in a system.

Fourth, this invention demonstrates the robustness of this epilepsy forewarning methodology over a variety of clinical conditions: digital and analog EEG from several clinical sites, data sampling at 200 and 512 Hz, raw EEG data precision between 10–12 bits, presence and lack of substantial noise in the raw EEG as well as other data quality difficulties, and use of a fixed channel (13) in the bipolar montage and use of a variety of clinically interesting channels in the 10/20 montage.

The robustness of the method means, in addition to its broad applicability, that it can be made widely available. Data acquisition and system monitoring can be accomplished under working conditions without the need for specialists. In the context of monitoring epilepsy conditions, this methodology will allow easy electrode placement by a patient in a non-clinical setting. Analogous advantages will inhere in the use of the invention under working conditions for other systems.

It is also noted that the current invention enables the manipulation of the data according to the invention on processor means that are relatively very small. The comparisons between the basecase cutsets and the testcase cutsets involve only those "bins" of the cutsets that are populated. This reduces the necessary memory by at least about 5,000-fold for the connected three-dimensional phase space (a six-dimensional space). Highly refined comparisons can then be accomplished on relatively small processors, ranging from programmed desk-top computers to specifically constructed integrated circuit panels.

The method of the invention, once disclosed, can be incorporated into apparatus. The apparatus can consist of either programmed general purpose memory and processing means, or can consist of specifically constructed circuitry dedicated to performing the necessary manipulations. Data acquisition means, such as the electrode from the bipolar montage, are connected to the processor means, which is dedicated to or programmed to perform the necessary calculations and comparisons. An output means is operatively attached to the processor means to provide an indication of the results of the process. In the case of detecting onset of an epileptic seizure, for example, the output may consist of a visual, auditory, or tactile signal to indicate that pre-seizure activity has been detected. The user can then take whatever steps his seizure protocol prescribes. Alternatively, the output signal may be graphical or textual, providing a monitoring capability for the state or condition being monitored. The latter may be preferred, for example, where the system being monitored is a tool, such as a drill bit, or a process such as a nuclear system. The signal, processor, memory, and output devices can vary widely, and include any known to those of skill in the art.

What is claimed is:

1. A method for monitoring a nonlinear process, the method comprising:

acquiring a set of channel data corresponding to at least one sensor for monitoring the process;

selecting cutsets of data from the set of channel data to form a basecase;

filtering artifacts from the selected cutsets of data to produce cutsets of artifact-filtered data for the basecase;

computing from the artifact-filtered data for each cutset in the basecase a set of connected phase space (PS) data comprising at least a first PS state and a second PS state connected to the first PS state;

computing distribution functions from the connected PS data for at least five cutsets of artifact-filtered data from the basecase;

computing at least one measure of dissimilarity (V) between a) a distribution function for a first one of the cutsets of artifact-filtered data from the basecase and b) a distribution function for a second one of the cutsets of artifact-filtered data from the basecase;

repeating the computation of the measure of dissimilarity (V) between distribution functions for non-identical pairings (i,j) of cutsets in the basecase until at least ten values ($V_{ij}$) are computed for the measure of dissimilarity (V);

computing an average (V) and a corresponding sample standard deviation ($\sigma_v$) from the at least ten values of dissimilarity ($V_{ij}$) for the basecase;

computing a $\chi^2$ statistic ($\Sigma(V_{ij}-V)^2/\sigma^2$) for the at least one measure of dissimilarity (V) for the cutsets of artifact-filtered data from the basecase;

identifying any outlier cutsets of artifact-filtered data from the basecase;

removing the outlier cutsets from the basecase; and recomputing the $\chi^2$ statistic and testing for outlier cutsets until no outlier cutset is identified.

2. The method of claim 1, further comprising:

acquiring additional data from said channel corresponding to at least one sensor for monitoring the process;

selecting a cutset of data from said channel data;

filtering artifacts from said cutset of additional channel data to produce a cutset of artifact-filtered data;

wherein the cutset of artifact-filtered data from the additional channel data defines a testcase;

computing from the artifact-filtered data for said testcase cutset, a set of connected phase space (PS) data comprising at least a first PS state and a second PS state connected to the first PS state;

computing a distribution function from the connected PS data for said testcase cutset of artifact-filtered data;

computing a set of dissimilarity values for at least one measure of dissimilarity (V), by comparing a distribution function derived from connected PS data for the testcase with each of the distribution functions derived for all non-outlier cutsets in the basecase;

obtaining an average ($V_t$) of the testcase dissimilarity over said set of dissimilarity values;

renormalizing said average testcase dissimilarity compared with the basecase, based on the formula, $U=|V_t-V|/\sigma_v$;

comparing said renormalized measure of dissimilarity to a predetermined threshold as one factor in anticipating a nonlinear event, and in response to anticipating a nonlinear event, providing a warning indication.

3. The method of claim 1, wherein the above acts are repeated for data acquired from a plurality of data channels corresponding to a plurality of sensors.

4. The method of claim 2, wherein the above acts are repeated for data acquired from a plurality of data channels corresponding to a plurality of sensors.

5. The method of claim 4, wherein at least two measures of dissimilarity ($L_c, \chi_c^2$) are computed between a) a distribution function derived from connected PS data for the testcase and b) each of the distribution functions computed for each of the non-outlier cutsets in the basecase.

6. The method of claim 1, further comprising acquiring additional basecase cutsets when more than four outlier cutsets are removed from the basecase.

7. The method of claim 2, further comprising:

computing from the artifact-filtered data for each cutset in the basecase a set of unconnected phase space (PS) data comprising a d-dimensional vector, where "d" is a number of phase space dimensions selected to represent the process;

computing distribution functions from the unconnected PS data for at least five cutsets of artifact-filtered data from the basecase;

computing at least one measure of dissimilarity (V) by comparing the distribution function for the unconnected PS data for a first one of the cutsets of artifact-filtered data from the basecase with the distribution function for the unconnected PS data for a second one of the cutsets of artifact-filtered data from the basecase;

repeating the computation of the measure of dissimilarity (V) for the unconnected PS data between distribution functions for non-identical pairings (i,j) of cutsets in the basecase until at least ten values ($V_{ij}$) are computed for the measure of dissimilarity (V);

computing an average (V) and a corresponding sample standard deviation ($\sigma_v$) from the at least ten values of dissimilarity ($V_{ij}$) for the basecase for the unconnected PS data;

computing a $\chi^2$ statistic ($\Sigma(V_{ij}-V)^2/\sigma^2$) for the measure of dissimilarity (V) for the unconnected PS data for the cutsets of artifact-filtered data from the basecase;

identifying any outlier cutsets of artifact-filtered data from the basecase;

removing the outlier cutsets from the basecase;

recomputing the $\chi^2$ statistic for the unconnected PS data and testing for outliers until no outlier cutset is identified;

computing from the artifact-filtered data for said testcase cutset, a set of unconnected PS data;

computing a distribution function from the unconnected PS data for said testcase cutset of artifact-filtered data;

computing a set of dissimilarity values for at least one measure of dissimilarity (V) for the unconnected PS data, by comparing a distribution function derived from unconnected PS data for the testcase with each of the distribution functions derived from the unconnected PS data for all non-outlier pairs of cutsets in the basecase;

obtaining an average ($V_i$) of the testcase dissimilarity over said set of dissimilarity values for the unconnected PS data;

renormalizing said average testcase dissimilarity compared with the basecase, based on the formula, $U=|V_i-V|/\sigma_v$;

comparing said renormalized measure of dissimilarity to a predetermined threshold as one factor in anticipating a nonlinear event, and in response to anticipating a nonlinear event, providing a warning indication.

8. The method of claim 7, wherein two measures of dissimilarity ($L_c, \chi_c^2$) are derived from distribution functions derived from the connected PS data and wherein the two measures of dissimilarity (L, $\chi^2$) are derived from the distribution functions derived from unconnected PS data;

renormalizing values for four measures of dissimilarity ($L_c, \chi_c^2, L, \chi^2$)

signaling a condition change in response to the four renormalized dissimilarity measures exceeding a predetermined threshold for a predetermined number of times; and repeating the aforementioned acts for a plurality of data channels.

9. A method for monitoring a nonlinear process, the method comprising:

acquiring a set of channel data corresponding to at least one sensor for monitoring the process;

selecting cutsets of data from the set of channel data to form a basecase;

filtering artifacts from the selected cutsets of data to produce cutsets of artifact-filtered data for the basecase;

computing from the artifact-filtered data for each cutset in the basecase a set of unconnected phase space (PS) data comprising a d-dimensional vector, where "d" is a number of dimensions selected to represent the process;

computing distribution functions from the unconnected PS data for at least five cutsets of artifact-filtered data from the basecase;

computing at least one measure of dissimilarity (V) between a) a distribution function for a first one of the cutsets of artifact-filtered data from the basecase and b) a distribution function for a second one of the cutsets of artifact-filtered data from the basecase;

repeating the computation of the measure of dissimilarity (V) between distribution functions for non-identical pairings (i,j) of cutsets in the basecase until at least ten values ($V_{ij}$) are computed for the measure of dissimilarity (V);

computing an average (V) and a corresponding sample standard deviation ($\sigma_v$) from the at least ten values of dissimilarity ($V_{ij}$) for the basecase;

computing a $\chi^2$ statistic ($\Sigma (V_{ij}-V)^2/\sigma^2$) for the measure of dissimilarity (V) for the cutsets of artifact-filtered data from the basecase;

identifying any outlier cutsets of artifact-filtered data from the basecase;

removing the outlier cutsets from the basecase;

recomputing the $\chi^2$ statistic and testing for outlier cutsets until no outlier cutset is identified;

acquiring additional data from said channel corresponding to at least one sensor for monitoring the process;

selecting a cutset of data from said channel data;

filtering artifacts from said cutset of additional channel data to produce a cutset of artifact-filtered data;

wherein the cutset of artifact-filtered data from the additional channel data defines a testcase;

computing from the artifact-filtered data for said testcase cutset, a set of unconnected phase space (PS) data comprising a d-dimensional vector, where "d" is a selected number of phase space dimensions selected to represent the process;

computing a distribution function from the unconnected PS data for said testcase cutset of artifact-filtered data;

computing a set of dissimilarity values for at least one measure of dissimilarity (V), by comparing a distribution function derived from unconnected PS data for the testcase with each of the distribution functions derived for all non-outlier pairs of cutsets in the basecase;

obtaining an average ($V_i$) of the testcase dissimilarity over said set of dissimilarity values;

renormalizing said average testcase dissimilarity compared with the basecase, based on the formula, $U=|V_i-V|/\sigma_v$;

comparing said renormalized measure of dissimilarity to a predetermined threshold as one factor in anticipating a nonlinear event, and in response to anticipating a nonlinear event, providing a warning indication.

10. The method of claim 9, wherein the above acts are repeated for data acquired from a plurality of data channels corresponding to a plurality of sensors.

11. The method of claim 9, further comprising:

computing from each cutset of artifact-filtered data, a set of connected phase space (PS) data derived from a first PS state, and from a second PS state connected to the first PS state;

computing distribution functions from the connected PS data for at least five cutsets of artifact-filtered data from the basecase;

computing at least one measure of dissimilarity (V) by comparing the distribution function for the connected PS data for a first one of the cutsets of artifact-filtered data from the basecase with the distribution function for the connected PS data for a second one of the cutsets of artifact-filtered data from the basecase;

repeating the computation of the measure of dissimilarity (V) for the connected PS data between distribution functions for non-identical pairings (i,j) of cutsets in the basecase until at least ten values ($V_{ij}$) are computed for the measure of dissimilarity (V);

computing an average (V) and a corresponding sample standard deviation ($\sigma_v$) from the at least ten values of dissimilarity ($V_{ij}$) for the basecase for the connected PS data;

computing a $\chi^2$ statistic ($\Sigma(V_{ij}-V)^2/\sigma^2$) for the measure of dissimilarity (V) for the connected PS data for the cutsets of artifact-filtered data from the basecase;

identifying any outlier cutsets of artifact-filtered data from the basecase;

removing the outlier cutsets in the basecase;

recomputing the $\chi^2$ statistic for the connected PS data and testing for outliers until no outlier cutset is identified;

computing from the artifact-filtered data for said testcase cutset, a set of connected PS data;

computing a distribution function from the connected PS data for said testcase cutset of artifact-filtered data;

computing a set of dissimilarity values for at least one measure of dissimilarity (V) for the connected PS data, by comparing a distribution function derived from connected PS data for the testcase with each of the distribution functions derived connected PS data for all non-outlier pairs of cutsets in the basecase;

obtaining an average ($V_t$) of the testcase dissimilarity over said set of dissimilarity values for the connected PS data;

renormalizing said average testcase dissimilarity compared with the basecase, based on the formula, $U=|V_t-V|/\sigma_v$;

comparing said renormalized measure of dissimilarity to a predetermined threshold as one factor in anticipating a nonlinear event, and in response to anticipating a nonlinear event, providing a warning indication.

12. A method for monitoring a nonlinear process via renormalized values, the method comprising:

computing an average value of dissimilarity (V) among unique pairings of non-identical, non-outlier cutsets of basecase data;

computing a sample standard deviation ($\sigma_v$), corresponding to said average dissimilarity;

computing an average value of dissimilarity for a plurality of testcase cutsets and the non-outlier basecase cutsets;

computing a renormalized value, $U=|V_t-V|/\sigma_v$, representing a number of standard deviations by which the average value of dissimilarity for the testcase varies from the average value of dissimilarity among non-outlier basecase cutsets;

repeating the previous four acts for all of the testcase cutsets for a plurality of dissimilarity measures;

signaling a condition change in response to all of the plurality of renormalized dissimilarity measures exceeding a predetermined threshold for a predetermined number of times; and repeating the aforementioned acts for a plurality of data channels.

* * * * *

UNITED STATES PATENT AND TRADEMARK OFFICE
CERTIFICATE OF CORRECTION

PATENT NO. : 6,484,132 B1
DATED : November 19, 2002
INVENTOR(S) : Lee M. Hively, Paul C. Gailey and Vladimir A. Protopopsescu It is certified that error appears in the above-identified patent and that said Letters Patent is hereby corrected as shown below:

Column 1,
Lines 24 and 25, should not be a new paragraph starting with "electrical transients".

Column 5,
Line 2, "33,1134-1140" should read -- 33, 1134-1140 --.

Column 6,
Lines 15 and 16, "$x_j$" should read -- $x_i$ --.

Column 8,
Line 46, "$(Q_i-R_j)^2$" should read -- $(Q_i-R_i)^2$ --.

Column 10,
Line 11, "symbol V" should read -- symbol $\underline{V}$ --.
Line 14, "$V_1$-V" should read -- $V_i$-$\underline{V}$ --.
Line 21, "ajoint" should read -- a joint --.

Column 12,
Line 5, "varies." should read -- varies --.

Column 13,
Line 57, "average, V" should read -- average, $\underline{V}$ --.
Line 59, "$(V_{ij}-V)^2$" should read -- $(V_{ij}-\underline{V})^2$ --.

Column 14,
Line 3, "of V" should read -- of $\underline{V}$ --.
Line 25, "often" should be -- of ten --.
Line 37, "V is" should be -- $\underline{V}$ is --.
Line 40, "$V_i$-V" should be -- $V_i$-$\underline{V}$ --.

Column 18,
Line 6, "average (V)" should read -- average ($\underline{V}$) --.
Line 9, "$(V_{ij}-V)^2$" should read -- $(V_{ij}-\underline{V})^2$ --.
Lines 42-43, "$V_i$-V" should read -- $V_i$-$\underline{V}$ --.

Column 19,
Line 15, "average (V)" should read -- average ($\underline{V}$) --.
Line 19, "$(V_{ij}-V)^2$" should read -- $(V_{ij}-\underline{V})^2$ --.
Lines 44-45, "$V_i$-V" should be -- $V_i$-$\underline{V}$ --.

UNITED STATES PATENT AND TRADEMARK OFFICE
CERTIFICATE OF CORRECTION

PATENT NO. : 6,484,132 B1
DATED : November 19, 2002
INVENTOR(S) : Lee M. Hively, Paul C. Gailey and Vladimir A. Protopopsescu It is certified that error appears in the above-identified patent and that said Letters Patent is hereby corrected as shown below:

Column 20,
Line 23, "average (V)" should read -- average ($\underline{V}$) --.
Line 26, "$(V_{ij}-V)^2$" should read -- $(V_{ij}-\underline{V})^2$ --.
Lines 59-60, "$V_i-V$" should read -- $V_i-\underline{V}$ --.

Column 21,
Line 21, "average (V)" should read -- average ($\underline{V}$) --.
Line 25, "$(V_{ij}-V)^2$" should read -- $(V_{ij}-\underline{V})^2$ --.

Column 22,
Lines 9-10, "$V_i-V$" should read -- $V_i-\underline{V}$ --.
Line 17, "(V) among" should read -- ($\underline{V}$) among --.
Line 25, "$V_i-V$" should read -- $V_i-\underline{V}$ --.

Signed and Sealed this

Second Day of December, 2003

JAMES E. ROGAN
*Director of the United States Patent and Trademark Office*